United States Patent
Gonsior

(10) Patent No.: US 7,122,101 B2
(45) Date of Patent: Oct. 17, 2006

(54) ELECTRICALLY CONDUCTIVE PLASTIC ELECTRODE SEALINGLY EMBEDDED IN AN INSULATING PLASTIC VALVE SEAT

(75) Inventor: Wolfgang Gonsior, Bodolz (DE)

(73) Assignee: Xomox International GmbH & Co., Lindau/Bodensee (DE)

( * ) Notice: Subject to any disclaimer, the term of this patent is extended or adjusted under 35 U.S.C. 154(b) by 837 days.

(21) Appl. No.: 10/352,180

(22) Filed: Jan. 28, 2003

(65) Prior Publication Data

US 2003/0221494 A1   Dec. 4, 2003

Related U.S. Application Data

(63) Continuation of application No. PCT/EP01/07620, filed on Jul. 4, 2001.

(30) Foreign Application Priority Data

Jul. 28, 2000   (DE) .............................. 200 13 142

(51) Int. Cl.
 *C25B 11/02* (2006.01)
 *C25B 11/04* (2006.01)
 *C25B 9/02* (2006.01)
(52) U.S. Cl. ................... 204/280; 204/404; 204/286.1; 204/287; 204/297.01
(58) Field of Classification Search ............... 204/280, 204/286.1, 287, 297.01, 404
See application file for complete search history.

(56) References Cited

U.S. PATENT DOCUMENTS

| | | |
|---|---|---|
| 4,388,834 A | 6/1983 | Schmoock |
| 5,380,422 A | 1/1995 | Negishi et al. |
| 5,865,971 A | 2/1999 | Sunkara |
| 5,925,830 A | 7/1999 | Schalk |
| 6,015,522 A | 1/2000 | Filanovsky et al. |
| 6,210,789 B1 * | 4/2001 | Hanrahan .................... 428/324 |
| 6,576,102 B1 * | 6/2003 | Rappin et al. ......... 204/403.14 |

FOREIGN PATENT DOCUMENTS

| | | |
|---|---|---|
| DE | 29 50 039 | 7/1981 |
| DE | 36 42 836 | 6/1988 |
| DE | 198 45 318 | 4/2000 |
| DE | 200 16 352 | 2/2001 |
| EP | 08 63 338 | 9/1998 |
| GB | 2 072 853 | 10/1981 |

OTHER PUBLICATIONS

International Search Report, Oct. 26, 2001.

* cited by examiner

*Primary Examiner*—Bruce F. Bell
(74) *Attorney, Agent, or Firm*—Crowell & Moring LLP

(57) ABSTRACT

A sensor including at least one electrode (3, 4) which is made of electrically conductive plastic and is connected to one end of an electrical conductor (5, 6). The electrode (3, 4) and conductor (5, 6) are surrounded by an insulating housing (2, 22), except that the electrode has an exposed surface (7, 8) for contacting an aggressive or corrosive medium inside the housing. The other end (11, 12) of the electrical conductor protrudes from the housing (2, 22). The housing (2, 22) is made of an electrically insulating plastic material which is joined to the electrode (3, 4) in a sealed manner. In a preferred embodiment, the housing (2, 22) forms a valve seat and seal for a bottom drain valve of a fluid container.

20 Claims, 5 Drawing Sheets

US 7,122,101 B2

ELECTRICALLY CONDUCTIVE PLASTIC ELECTRODE SEALINGLY EMBEDDED IN AN INSULATING PLASTIC VALVE SEAT

CROSS REFERENCE TO RELATED APPLICATIONS

This application is a continuation of international patent application no. PCT/EP01/07620, filed Jul. 4, 2001 designating the United States of America, and published in German as WO 02/10733, the entire disclosure of which is incorporated herein by reference. Priority is claimed based on Federal Republic of Germany patent application no. DE 200 13 142.7, filed Jul. 28, 2000.

BACKGROUND OF THE INVENTION

The present invention relates to an apparatus comprising at least one electrically conductive plastic electrode substantially embedded in a surrounding insulating housing.

Apparatus of this type are known from U.S. Pat. No. 4,368,834, German Patent Application 29 50 039 and U.S. Pat. No. 5,925,830. These devices are configured as electromagnetic flow rate meters and contain two electrodes in diametrically opposing recesses of a tubular housing, which are tightly bonded to the insulating plastic of an internal lining or of the entire tube. The electrodes are made of electrically conductive plastic and, except for the exposed surfaces, which are in contact with the medium flowing through the tube, are enclosed in the insulating plastic. The respective electrode extends radially over the entire thickness of the wall of the housing and/or tube from the inside to the outside and is electrically conductively connected to an electric conductor, which is constructed as a wire or pin in a radially external region. The electric conductor is not enclosed in insulating housing, but rather leads from the radial external surface of the electrode to the outside. According to German Patent Application 29 50 039, a metal mesh is also attached to the electrical conductor and an electrical insulation layer is also provided, the electrically insulating housing also not enclosing the electrical conductor in this case. There is no further information in the three cited publications for other fixing or support of the electrical conductor in relation to the housing. The electrode is exclusively fixed by the housing and additional means for the electrical conductor are not provided. Problems may arise because of this, both in manufacturing, while the electrical conductor and the electrode are pressed in or injection molded, and in use, due to the forces acting on the electrical conductor from the outside, the connection between the electrical conductor and the electrode being disturbed. In addition, the housing, which is configured as a tube, requires a significant amount of space.

An apparatus is known from German Patent 198 45 318, which is configured as an electrochemical oxygen sensor and contains a measurement electrode and an air-oxygen electrode. The measurement electrode comprises a gas-permeable, polymeric, perfluorinated diffusion membrane, which is coated at least partially on one side using a mixture made of a noble metal and PTFE (polytetrafluoroethylene). The diffusion membrane is exposed to the ambient atmosphere and, together with the electrodes described and an electrolyte, is positioned in the sensor housing, which is made of porous PTFE, in order to allow oxygen exchange and pressure equalization independent of position. The measurement electrode and the diffusion membrane are constructed with circular surfaces and have an external diameter of a magnitude of 2 to 50 mm. Since, in such an oxygen sensor, the oxygen must get through the gas-permeable diffusion membrane and the porous housing to reach the inside of the housing to the electrodes positioned there, the possible uses are restricted, use for fluids or mediums which are aggressive and/or under pressure not being possible without something further.

Modern production methods for chemical, biochemical, and pharmaceutical products, food products, or the like react more and more sensitively to changes in the production conditions, so that high precision during the production is necessary. With increasing automation of the production methods, copious information is necessary for detecting the properties of the often aggressive or corrosive fluids or media and the process conditions, this referring above all to the pressure, the temperature, and state of the fluid or medium. To detect information of this type, electrodes are used, which are often positioned directly in the region of the fluid or medium and come into contact with them. Electrical conductors, which must lead out of the region containing the fluid or medium to the outside and/or must be extended through the respective machine or facility parts, are required for using the electrodes and for relaying the information detected to associated electrical or electronic analysis devices.

SUMMARY OF THE INVENTION

Accordingly, it is an object of the present invention to provide an improved device of the type described above.

Another object is to provide a device in which the electrical conductor, including the electrode, is more securely fixed in place.

A further object of the invention is to provide a device which may be integrated as a compact component into an apparatus and connected to the apparatus without any problems.

These and other objects are achieved in accordance with the present invention by providing an apparatus comprising at least one electrically conductive plastic electrode substantially embedded in a surrounding insulating housing and connected to a first end of an electrical conductor also embedded within the insulating housing and extending out of said housing to an exposed second end; the electrode having an exposed surface for contacting a medium in said housing, and the housing surrounding said electrode being comprised of insulating plastic sealingly bonded to said electrode, in which the electrical conductor is constructed as a support for the electrode or an electrode support is associated with the electrical conductor, and the housing comprises a radial flange through which the electrical conductor is extended such that the second end of the conductor emerges from a radially outer surface of the flange.

The apparatus of the present invention comprises at least one electrode, which is made of an electrically conductive plastic, particularly fluorinated plastic having electrically conductive particles intermixed therein, and which is arranged at one end of an electrical conductor. The electrode is embedded together with the conductor in an insulating housing or a body, which is made, at least in the region of the electrode, from an insulating plastic material, particularly from virgin PTFE. In the region which comes into contact with the fluid or medium, however, the electrode is free of the insulating plastic of the housing or the housing region which otherwise envelops the electrode. The electrical conductor is preferably made of metal and is not guided through the housing and/or the housing wall, but rather only one end of the conductor leads out of the housing, and otherwise the conductor is integrated into the housing with the electrode positioned on the other end. Alternatively, the electrical conductor is made of electrically conductive plastic and is constructed in one piece with the electrode. The housing, with integrated electrode and conductor, forms a compact component which is advantageously a part of a larger device, particularly a valve. The electrically non-conductive plastic of the housing is bonded tightly to the electrode, particularly through melting or welding, preferably liquid-tight and/or gas-tight and/or pressure-tight. The electrode has an exposed surface which comes into contact with the fluid or medium, and the electrical conductor extends through the housing to the outside, in order to facilitate electrical connection there to measurement devices or the like.

According to the present invention, the electrical conductor may be configured as a support body for the electrode and is positioned in the way required together with the electrode in the housing, which at least partially encloses the electrode and the conductor, during manufacturing, particularly through injection molding, compression, or casting. At least one support element is preferably associated with the electrical conductor for positioning it in the housing. The support element is also preferably made of an electrically non-conductive plastic, especially from the same or a similar plastic as the housing. During the production of the device, the electrical conductor, on whose inner end the electrode is arranged, is positioned using the support element(s) in the forming tool, particularly an injection mold or casting mold, the plastic forming the housing being introduced into the tool described in a following method step and particularly being injected or cast. The plastic introduced in this way into the cavity of the forming tool forms an intimate, tight bond with the electrically conductive plastic of the electrode, particularly through melting or welding. In this way, a molecular boundary layer or joint zone arises in which molecules of the plastic of the housing and electrode mesh with one another and/or form chains through which an integral unit between the electrode and the housing or the housing region enveloping the electrode is produced. Furthermore, the housing or the body advantageously contains a support body, at least approximately completely enclosed by plastic, which serves to stabilize and/or rigidify the device. If the device is configured as an annular body, the support body is arranged inside the housing and cast into the plastic of the housing. In such case, the support body is advantageously constructed as a bushing and/or simultaneously as an annular body.

In one preferred embodiment of the present invention, the electrode is manufactured using a method in which the electrode material, provided as a powder, is first pressed onto one end of the electrical conductor, which is preferably made of metal, and compressed into a solid body, so that the resulting premanufactured electrode preferably encloses the end of the electrical conductor. The electrical conductor is preferably perforated on the end described, so that the electrode material penetrates through the perforations and the heat transfer and/or the strength of the bond between the electrode and the electrical conductor is advantageously optimized.

In a further method step, the electrode, with the conductor, is embedded in the plastic of the housing, particularly by a casting method or injection molding method using a mold having a mold cavity in which the electrode, including the conductor, is positioned, and into which the plastic of the housing is introduced. For this purpose, at least one support element is advantageously used, which is configured for clamping and positioning the electrical conductor within the mold cavity. Furthermore, a support body may advantageously be positioned in the cavity of the mold or forming tool, which, like the electrode and the electrical conductor, is completely enclosed by the plastic when the plastic is introduced into the mold, so that only the one exposed end of the electrical conductor extends out of the plastic, i.e., is not surrounded by the plastic of the housing.

The apparatus is preferably integrated as a compact component in a larger assembly or device, particularly in valves, flange connections, or similar devices. The apparatus is particularly advantageously a part of a valve seat, so that practically no additional expenditure for apparatus is necessary for detecting the necessary information and/or process data of the production method.

In a particularly advantageous embodiment, the apparatus of the present invention may be integrated as a component of a bottom drain valve of a receptacle or reactor, in which the fluid or medium used is processed in accordance with greatly different methods. These types of reactors, valves, or other assemblies are often provided with a plastic lining, particularly made of fluorinated plastics, such as, in particular, PTFE (polytetrafluoroethylene), FEP (fluoroethylene propylene), PFA (perfluoroalkoxyl), PVDF, PTFES, FEPS, or comparable plastics. The electrode and/or the housing enclosing the electrode and the electrical conductor are preferably made of or contain these types of plastics, particularly fluorinated plastics.

BRIEF DESCRIPTION OF THE DRAWINGS

The invention will be described in further detail hereinafter with reference to illustrative preferred embodiments shown in the accompanying drawings, in which.

DETAILED DESCRIPTION OF PREFERRED EMBODIMENTS

Figure 1:
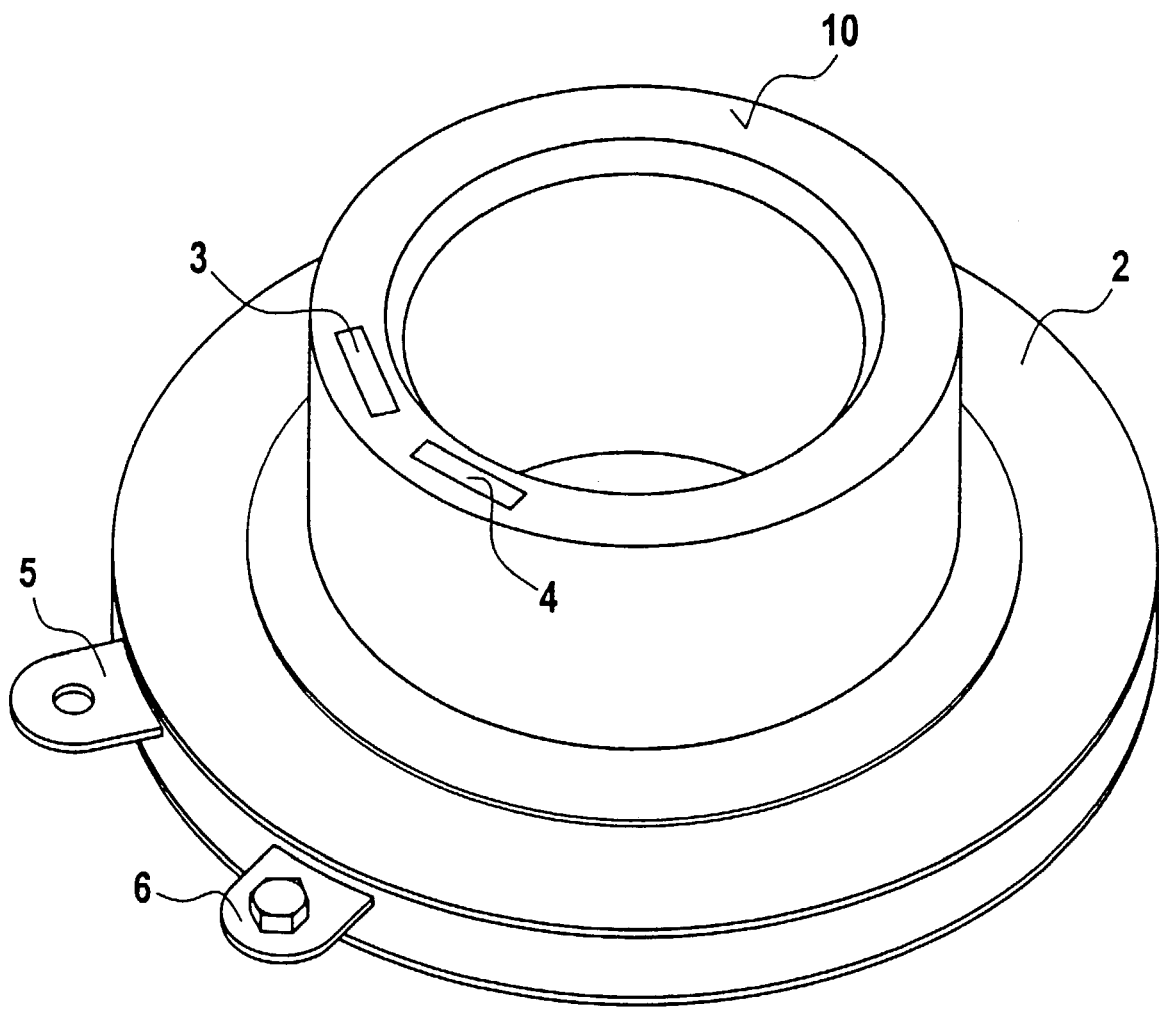
FIG. 1 is a perspective view of the an embodiment of the invention constructed as a valve seat.

FIG. 1 shows the apparatus according to the present invention, which comprises a housing or body 2 made of plastic, particularly made of fluorinated plastic, such as PTFE, FEP, PFA, PTFES, FEPS, or PVDF. In the plastic described and/or housing or body 2, two electrodes 3, 4, and electrical conductors 5, 6 electrically connected thereto, are embedded, which are particularly made of metal and whose ends lead out of housing 2, in order to allow electrical connection to a suitable analysis device or the like. Only the surfaces of both electrodes 3, 4 facing the medium or fluid to be sensed, which are free of the insulating plastic of the housing, may be seen. According to the present invention, the device is configured as a valve seat of a valve (See FIG. 6).

Figure 2:
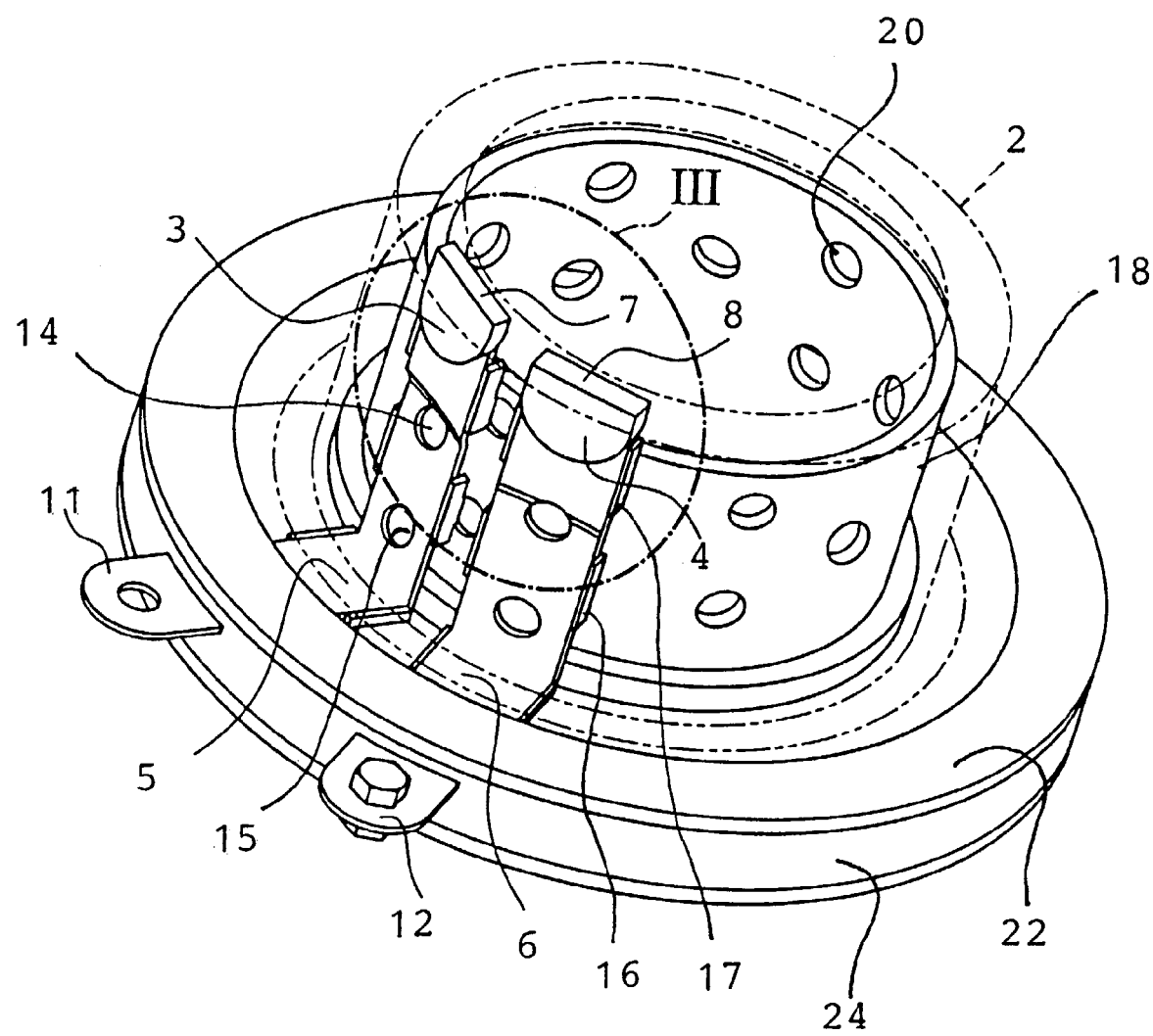
FIG. 2 is a view similar to FIG. 1, in which the housing is illustrated as partially transparent.

FIG. 2 shows a view of the device, the housing being illustrated as partially transparent so that the electrical conductors 5, 6 and electrodes 3, 4, which are practically completely enclosed by the impermeable plastic of the housing, are easily visible. Electrodes 3, 4 enclose the inner end of electrical conductors 5, 6 and are bonded to them permanently and electrically conductively. Electrodes 3, 4, which are made at least partially of electrically conductive plastic, preferably contain electrically conductive particles which allow current flow through electrodes 3, 4 and attached electrical conductors 5, 6. Electrodes 3, 4 are embedded pressure-tight and/or liquid-tight in the plastic of housing 2 and are preferably bonded by melting and/or welding. This bond is preferably produced using a suitable forming tool during the manufacture of the housing, particularly through plastic injection molding, compression, or casting, so that electrodes 3, 4 and electrical conductors 5, 6 are enveloped by the plastic of the impermeable housing and the plastics are melted into and/or welded onto one another in the boundary surfaces of the electrode and of the housing.

Exposed surfaces 7, 8 of both electrodes 3, 4 lie in an annular axial end surface 10 of the device and/or of the valve seat and, according to the present invention, are positioned next to one another around the circumference at a predetermined interval. Exposed surfaces 7, 8 may advantageously be processed jointly with the processing of annular surface 10. Annular surface 10 comes into contact with the fluid and/or medium to be sensed, and therefore both exposed surfaces 7, 8 as well and, as a consequence of this, an electrical current may flow between the two electrodes in accordance with the properties of the fluid or medium, so that an electrical signal may be picked up at exposed ends 11, 12 of the electrical conductors, which extend out of the housing. The bond of the electrodes to the surrounding housing region is preferably implemented as pressure-tight in such a way that pressure differentials between an inner space of a device, particularly a valve, associated with surfaces 7, 8, and an outer space containing exposed ends 11, 12 do not lead to leaks. Electrical conductors 5, 6 contain recesses or openings 14, 15 for optimized anchoring in the plastic of enveloping housing 2.

Electrical conductors 5, 6 are also associated with support elements 16, 17, which are particularly advantageously configured for positioning electrical conductors 5, 6 in the complete device and/or in a forming tool, particularly an injection mold or casting mold. Support elements 16, 17 are preferably made of virgin PTFE or of a plastic identical or similar to that of the housing, so that an integral bond is ensured after the production of the device, as well as permanent and exact positioning. Support elements 16, 17 are partially tailored to the external contour of electrical conductors 5, 6 and are configured like a type of clip or plug-in connection in order to ensure proper positioning in the forming tool and/or the housing.

Furthermore, the apparatus advantageously may comprise a support body 18, which is at least approximately, preferably completely, embedded in the plastic of housing 2. In the illustrated, preferred annular implementation of the device, support body 18 is configured as an essentially annular body. Support body 18 is made of a material which is more stable and/or stiffer than the plastic of the housing, particularly metal. Furthermore, support body 18, which preferably is constructed as an annular body or bushing, contains recesses or openings 20. Support elements 16, 17 engage using appropriately configured projections in recesses 20 described, through which exact positioning of electrical conductors 5, 6, and therefore of electrodes 3, 4, is advantageously ensured in the forming tool and ultimately in housing 2.

Furthermore, in a particularly preferred embodiment of the apparatus of the present invention, the housing comprises a flange 22, which is advantageously configured for mounting and fixing the device, preferably between flanges of associated machine or facility parts, especially of a valve. Exposed ends 11, 12 of conductors 5, 6 preferably extend from the preferably cylindrical external surface 24 of flange 22. If flange 22 is positioned between two flanges of the associated machine or facility parts, electrical lines for connection to an analysis device or the like may be connected to exposed ends 11, 12 which lead out in this way.

Figure 3:
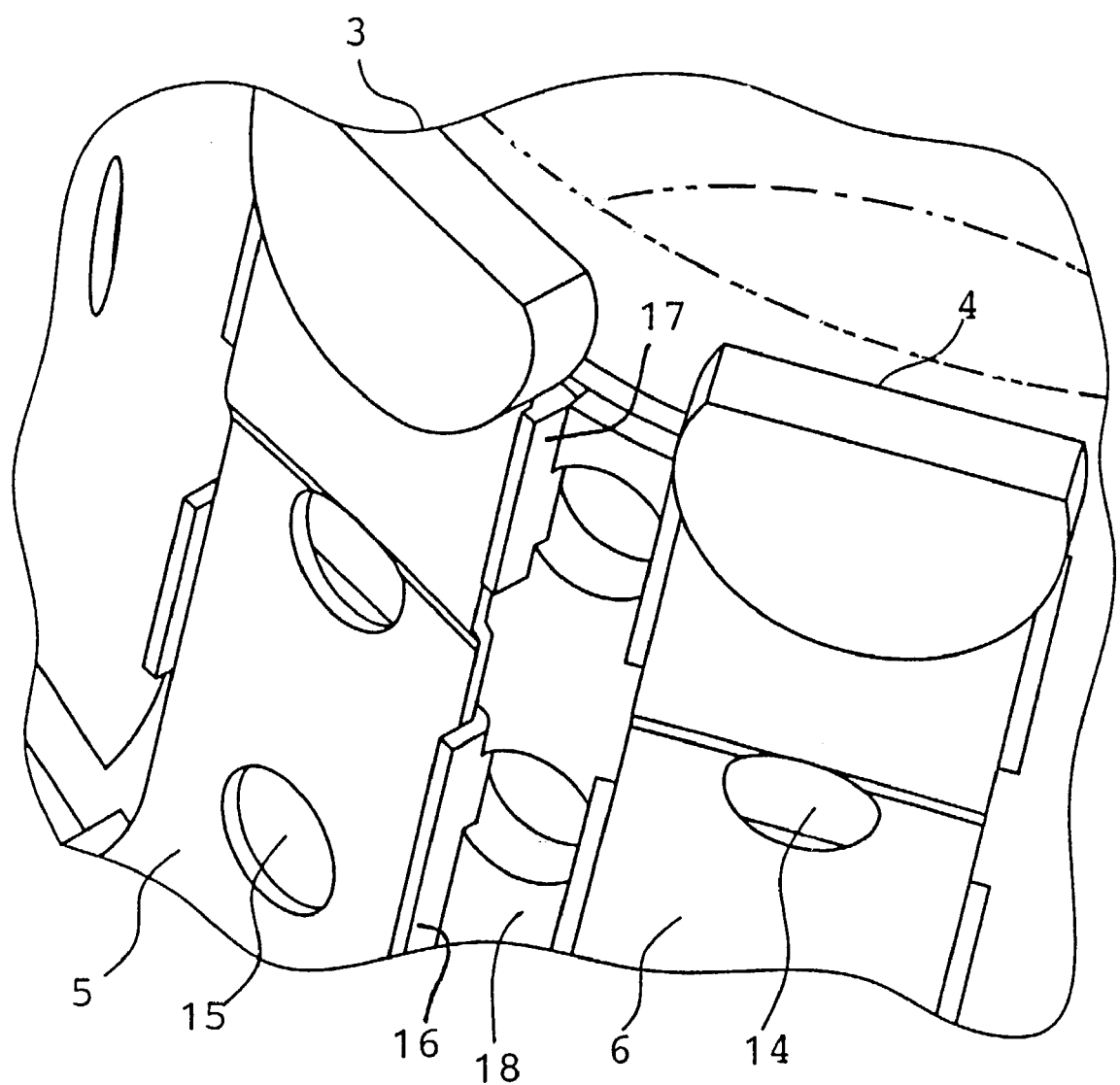
FIG. 3 is an enlarged view of detail III of FIG. 2.

FIG. 3 shows both electrodes 3, 4 and part of electrical conductors 5, 6 enlarged and in detail. Electrical conductors 5, 6 advantageously contain recesses in the form of openings 14, 15, which are filled up by the plastic of the housing, so that permanent and stable anchoring is ensured. Furthermore, support elements 16, 17 and annular support body 18 may be easily seen in this drawing figure.

Figure 4:
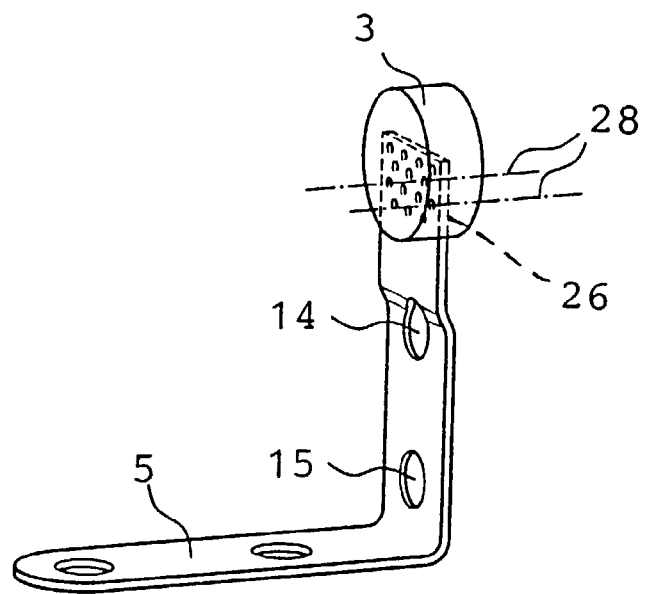
FIG. 4 is a view of the electrode including the electrical conductor.
Figure 5:
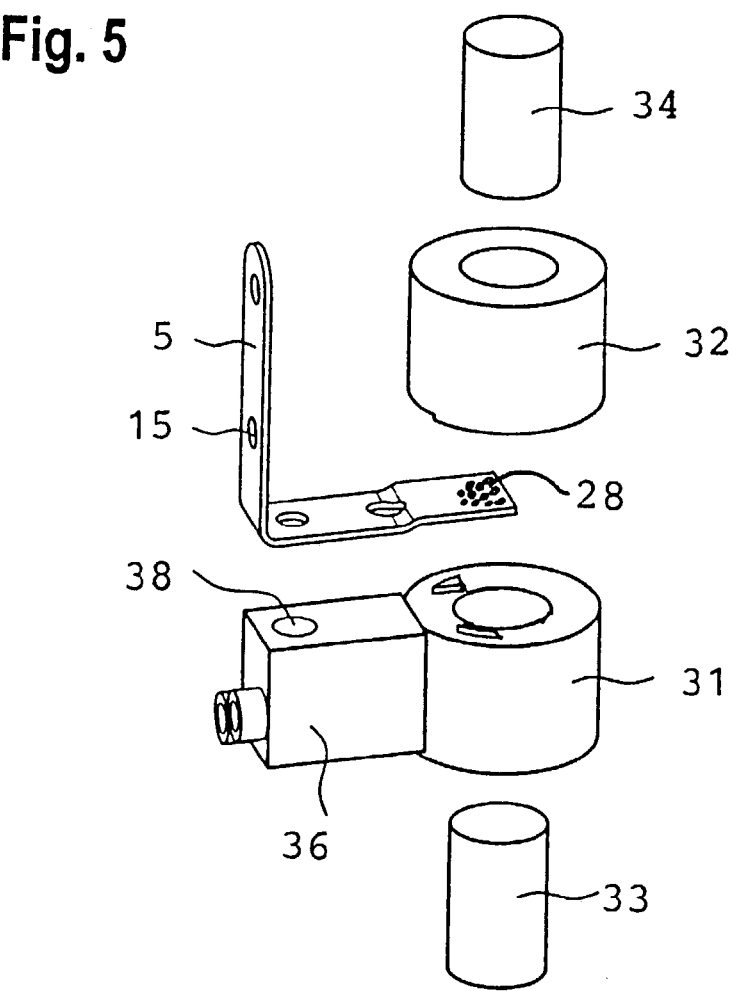
FIG. 5 is a schematic illustration of an apparatus for producing the electrode and simultaneously connecting it to the electrical conductor.

FIG. 4 shows electrode 3, made of fluorinated plastic, in which electrically conductive particles are embedded. As is shown, the electrode encloses one end of electrical conductors 5 and is permanently bonded thereto. Inner end 26 of conductors 5 is advantageously perforated in the vicinity of electrode 3, as is indicated by broken lines 28. The plastic of electrode 3 penetrates these perforations 28, so that not only is a stable and permanent bond ensured, but also the heat transfer and the electrical conductivity between electrode 3 and electrical conductor 5 are significantly improved.

A method and a device useful for producing the electrode and its simultaneous bond to electrical conductor 5 are described in the following. The device contains two cylinders 31, 32, into which two pistons 33, 34 may be inserted. After the partial insertion of lower piston 33 into cylinder 31, as shown in the drawing, the powdered plastic for the electrode is introduced into the upper free space and the electrode is inserted on top of cylinder 31 as shown, the plastic powder also being applied over the end of electrical conductor 5. Lower cylinder 31 is positioned on a support device 36, which has a fixing element for electrode 5, fixing element 38 engaging in recess 15 of electrical conductor 5.

Subsequently, both cylinders 31, 32 and both pistons 33, 34 are moved toward one another. Pistons 33, 34 are components of a press, which, using high pressure, compresses the plastic powder, including the electrically conductive particles, into an impermeable and solid electrode. During compression, heat is also advantageously supplied, for example via an electrical heating device integrated in cylinder 31 (not shown here). As a consequence of the heating to a selectable temperature, the initially powdered plastic is plasticized, so that ultimately a compact electrode which is integrally bonded to electrical conductor 5, preferably made of metal, is produced.

In an alternative embodiment, the electrical conductor is made of an electrically conductive plastic, like the electrode. In this case, the electrical conductor may be bonded to the electrode and form an integral unit analogously to the embodiments above. Furthermore, in a preferred refinement, the electrical conductor and the electrode may be constructed in one piece and produced jointly in a uniform method, particularly a pressing method, analogously to the production method described above for the electrode, from powdered, electrically conductive plastic. In this embodiment, the support elements and/or the support body described above are of particular significance, for example for the case in which the electrically conductive plastic has insufficient stiffness and intrinsic stability. Using the support elements and/or the support body, reliable positioning of the electrical conductor with the electrode molded on in one piece is ensured, above all during production.

Figure 6:
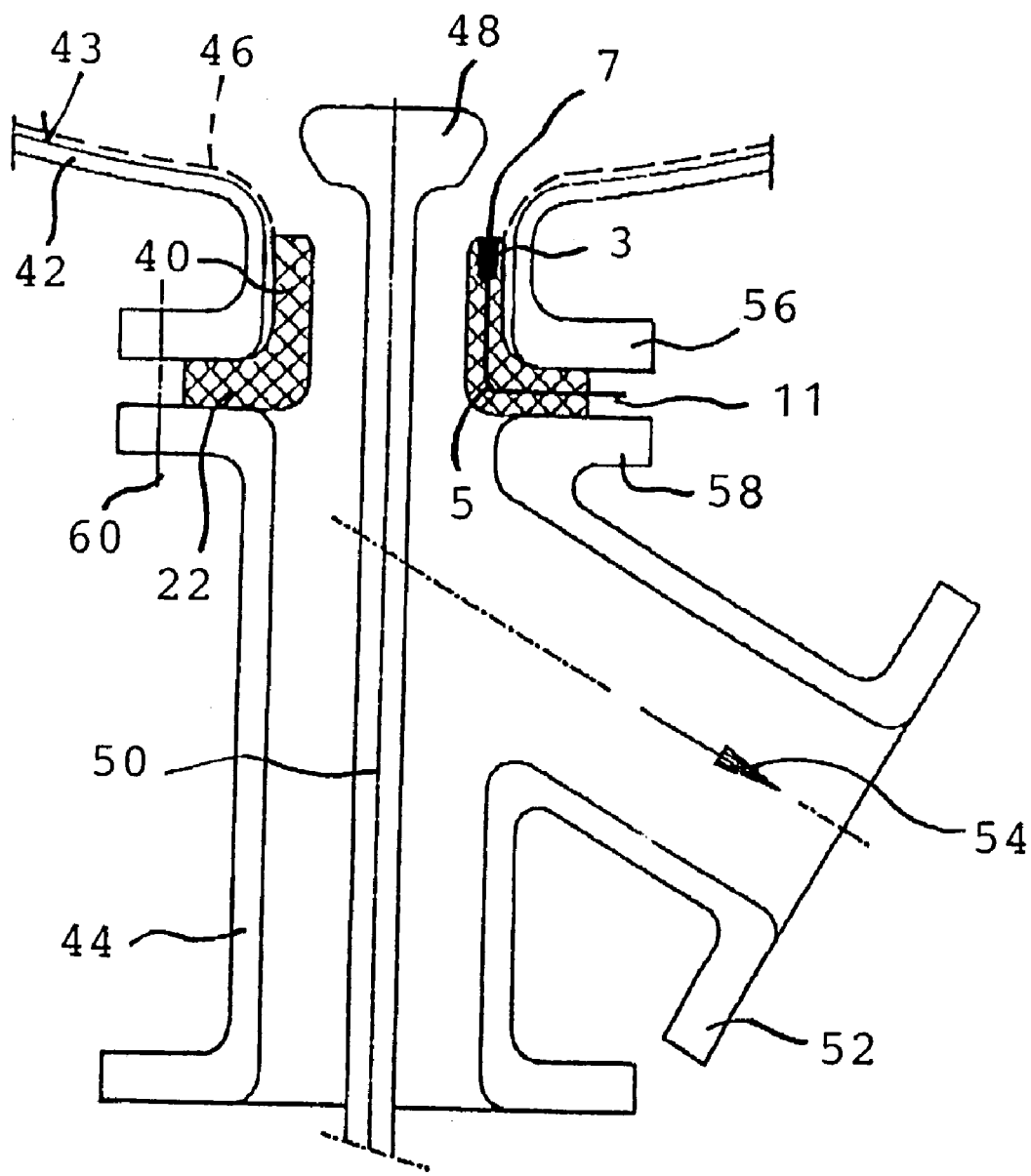
FIG. 6 is a schematic axial section through a valve having a valve seat constructed as an apparatus according to the invention.

FIG. 6 schematically shows an axial section of a preferred embodiment of the device configured as a valve seat or seat ring 40. The valve is configured as a bottom drain valve of a receptacle or reactor 42, which is only partially shown here and whose inner surface 43 is provided with a plastic lining 46, indicated by broken lines. The valve contains a valve body 48, which is axially movable in a known way in the direction of an axis 50. Valve body 48 is illustrated in the open position, so that a medium or fluid in the receptacle may flow out through an outlet 52 in the direction of arrow 54. At the lower end of valve housing 44, a device or a drive (not shown) for axially moving the valve body 48 is positioned in a known way, in order, if necessary, to move valve body 48 downward from the open position illustrated into the sealed position in which the valve body 48 is pressed against valve seat 40 to form a seal. Receptacle 42 has a flange 56 at the bottom, to which a flange 58 of valve housing 44 is connected, particularly using screws as shown by broken line 60. Flange 22 of valve seat 40 is positioned and tightly clamped between flanges 56 and 58 described. Exposed surface 7 of electrode 3 is oriented toward the inside of receptacle 42, so that the medium stored in the receptacle may be detected and sensed without difficulty. Exposed end 11 of electrical conductor 5 projects radially outwardly into the annular space between the two flanges 56 and 58, so that an electrical line to an analysis unit or the like may be connected there without any problems.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations falling within the scope of the appended claims and equivalents thereof.

What is claimed is:

1. An apparatus comprising at least one electrically conductive plastic electrode substantially embedded in a surrounding insulating housing and connected to a first end of an electrical conductor also embedded within the insulating housing and extending out of said housing to an exposed second end; said electrode having an exposed surface for contacting a medium in said housing; said housing surrounding said electrode being comprised of insulating plastic tightly bonded to said electrode; wherein said electrical conductor is constructed as a support for said electrode or an electrode support is associated with the electrical conductor, and said housing comprises a radial flange through which the electrical conductor is extended such that said second end of the conductor emerges from a radially outer surface of the flange.

2. An apparatus according to claim 1, wherein said flange is an annular flange with a cylindrical outer surface.

3. An apparatus according to claim 1, wherein the medium in said housing is a corrosive liquid.

4. An apparatus according to claim 1, wherein said housing is made entirely of insulating plastic material.

5. An apparatus according to claim 1, wherein the conductive electrode is comprised of a normally insulating, fluid-impermeable plastic material containing conductive particles distributed throughout.

6. An apparatus according to claim 1, wherein the plastic of the electrode is a fluorine-containing synthetic resin material.

7. An apparatus according to claim 1, wherein the plastic of the housing is a fluorine-containing synthetic resin material.

8. An apparatus according to claim 1, wherein the electrode and the electrical conductor are integrated into the housing during manufacture of the housing, whereby a sealed joint is formed between the plastic of the electrode and the plastic of the housing.

9. An apparatus according to claim 1, wherein the bond between the electrode and the housing is fluid-tight or pressure-tight.

10. An apparatus according to claim 1, wherein said housing is a valve seat for a valve.

11. An apparatus according to claim 10, wherein the exposed surface of the electrode is positioned in an annular surface of the valve seat.

12. An apparatus according to claim 1, wherein the electrical conductor is provided with perforations in the vicinity of the electrode, which are filled by the plastic of the electrode.

13. An apparatus according to claim 1, wherein the electrical conductor is made of metal or electrically conductive plastic, and the electrical conductor and the electrode together form an integral or one-piece unit.

14. An apparatus according to claim 1, wherein the electrical conductor is mounted in a support element made of an electrically insulating plastic.

15. An apparatus according to claim 1, wherein the electrical conductor is supported by a support body having a higher rigidity or strength than the plastic of the housing.

16. An apparatus according to claim 1, wherein the electrode, except for the exposed surface for contacting the medium in the housing, is enclosed around its entire outer contour by the electrically non-conductive plastic of the housing.

17. An apparatus according to claim 1, wherein the conductive plastic of electrode is bonded sealingly to the insulating plastic of the housing by fusion or welding.

18. An apparatus according to claim 1, wherein the exposed surface of the electrode lies essentially in the same plane as a surface of the housing.

19. An apparatus according to claim 18, wherein said surface of the housing is an axial end face of a tubular housing.

20. An apparatus according to claim 1, wherein said apparatus is an electrical sensor.

* * * * *